United States Patent
Capodieci et al.

(10) Patent No.: US 7,310,155 B1
(45) Date of Patent: Dec. 18, 2007

(54) EXTRACTION OF TOOL INDEPENDENT LINE-EDGE-ROUGHNESS (LER) MEASUREMENTS USING IN-LINE PROGRAMMED LER AND RELIABILITY STRUCTURES

(75) Inventors: Luigi Capodieci, Santa Cruz, CA (US); Amit P. Marathe, Sunnyvale, CA (US); Bhanwar Singh, Morgan Hill, CA (US); Ramkumar Subramanian, Sunnyvale, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 467 days.

(21) Appl. No.: 10/958,149

(22) Filed: Oct. 4, 2004

(51) Int. Cl.
  *G01B 11/04* (2006.01)
  *G01B 11/14* (2006.01)
(52) U.S. Cl. .................... 356/625; 356/363; 356/237.4
(58) Field of Classification Search .. 356/237.1–237.5, 356/600–540; 250/310–311; 430/30, 296, 430/942; 382/149, 154
See application file for complete search history.

(56) References Cited

U.S. PATENT DOCUMENTS

| | | | |
|---|---|---|---|
| 6,697,153 B1* | 2/2004 | Wright et al. | 356/237.4 |
| 6,873,720 B2* | 3/2005 | Cai et al. | 382/149 |
| 6,929,892 B2* | 8/2005 | Shishido et al. | 430/30 |
| 6,955,078 B2* | 10/2005 | Mancevski et al. | 73/105 |
| 6,980,937 B2* | 12/2005 | Hayes | 703/2 |
| 7,003,149 B2* | 2/2006 | Benesch et al. | 382/145 |
| 7,046,375 B2* | 5/2006 | Bischoff et al. | 356/600 |
| 7,049,589 B2* | 5/2006 | Yamaguchi et al. | 250/310 |
| 7,064,846 B1* | 6/2006 | Amblard et al. | 356/636 |
| 7,184,152 B2* | 2/2007 | Brill | 356/636 |

* cited by examiner

*Primary Examiner*—Sang H. Nguyen
(74) *Attorney, Agent, or Firm*—Amin, Turocy & Calvin LLP

(57) ABSTRACT

A system that facilitates extraction of line edge roughness measurements that are independent of proprietorship of a metrology device comprises a structure patterned onto silicon with known line edge roughness values associated therewith. A metrology device obtains line edge roughness measurements from the structure, and a correcting component generates an inverse function based upon a comparison between the known line edge roughness values and the measured line edge roughness values. The metrology device can thereafter measure line edge roughness upon a second structure patterned on the silicon, and the inverse function can be applied to such measured line edge roughness values to enable obtainment of line edge roughness measurements that are independent of proprietorship of the metrology device.

16 Claims, 11 Drawing Sheets

EXTRACTION OF TOOL INDEPENDENT LINE-EDGE-ROUGHNESS (LER) MEASUREMENTS USING IN-LINE PROGRAMMED LER AND RELIABILITY STRUCTURES

TECHNICAL FIELD

The present invention generally relates to monitoring line-edge roughness during semiconductor processing, and in particular to calibrating a metrology tool through utilization of programmed line-edge-roughness structures.

BACKGROUND

In the semiconductor industry, there is a continuing trend toward higher device densities. To achieve these high densities, there has been and continues to be efforts toward scaling down device dimensions (e.g., at submicron levels) on semiconductor wafers. In order to accomplish such high device packing density, smaller and smaller feature sizes are required in integrated circuits (ICs) fabricated on small rectangular portions of the wafer, commonly known as dies. This can include width and spacing of interconnecting lines, spacing and diameter of contact holes, surface geometry such as corners and edges of various features as well as surface geometry of other features. To scale down device dimensions, more precise control of fabrication processes are required. The dimensions of and between features can be referred to as critical dimensions (CDs). Reducing CDs, and reproducing more accurate CDs facilitates achieving higher device densities through scaled down device dimensions and increased packing densities.

The process of manufacturing semiconductors or ICs typically includes numerous steps (e.g., exposing, baking, developing), during which hundreds of copies of an integrated circuit may be formed on a single wafer, and more particularly on each die of a wafer. In many of these steps, material is overlayed or removed from existing layers at specific locations to form desired elements of the integrated circuit. Generally, the manufacturing process involves creating several patterned layers on and into a substrate that ultimately forms the complete integrated circuit. This layering process creates electrically active regions in and on the semiconductor wafer surface.

Lithography is one particular process utilized in semiconductor processing and/or manufacturing. Lithography generally refers to processes for pattern transfer between various media. It is a technique used for integrated circuit fabrication in which a silicon slice, the wafer, is coated uniformly with a radiation-sensitive film, the photoresist. Thereafter, an exposing source (such as optical light, X-rays, or an electron beam) illuminates selected areas of the surface through an intervening master template (e.g., a photoresist mask) for a particular pattern. The lithographic coating is generally a radiation-sensitized coating suitable for receiving a projected image of the subject pattern. Once the image is projected, it is indelibly formed in the coating. The projected image may be either a negative or a positive of the subject pattern. Exposure of the coating through the photoresist mask causes a chemical transformation in the exposed areas of the coating thereby making the image area either more or less soluble (depending on the coating) in a particular solvent developer. The more soluble areas are removed in the developing process to leave the pattern image in the coating as less soluble polymer. The resulting pattern image in the coating, or layer, may be at least one portion of a semiconductor device that contributes to the overall structure and function of the device.

Due to continuous shrinking of design dimensions, precision during patterning is of increasing importance. As these design dimensions are reduced, monitoring, controlling, and correcting line edge roughness (LER) resident upon a semiconductor substrate is becoming essential to maintain adequate device yield. LER refers to a measurement of irregularity on a semiconductor substrate from a perfectly rectilinear profile, wherein such irregularity can occur during patterning. Conventional systems and/or methodologies for measuring and/or correcting LER are proprietary, and they utilize independently developed measurement algorithms. Thus, differing measurement/correction tools will provide dissimilar LER measurements for a single line/structure. Correction measures therefore will be dependent upon the metrology tool, and such non-uniformity between metrology tools can lead to inefficient design and manufacturing of integrated circuits. For example, a structure can be measured by three disparate metrology tools, the tools finding the roughness to be of measurement M1, M2, and M3, respectively. M1 may be within manufacturing specifications, while M2 and M3 may be outside such specifications. Because one fab includes a large number of metrology tools, determining an amount of correction for different tools can require substantial resources and result in lack of efficiency during integrated circuit manufacturing. As such, metrology tools and algorithms cannot be compared and correlated with manufacturing device performance.

Accordingly, there is a need in the art for a tool independent system and/or methodology for measuring and correcting line edge roughness.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its purpose is merely to present some concepts of the invention in a simplified form as a prelude to the more detailed description that is presented later.

The present invention provides a system and/or methodology that facilitates obtainment of line edge roughness values that are independent of a metrology tool. For example, the present invention can be employed to effectively de-convolve proprietary algorithms that are utilized by metrology devices. One or more structures with known line edge roughness values associated therewith are patterned onto a wafer, and these known line edge roughness values are stored for later retrieval. For example, the structures can include a square wave structure, a rectangular wave structure, and/or a sawtooth wave structure. These structures can have a particular wavelength, amplitude, and or pitch that can be known prior to the metrology device measuring such values. In accordance with one exemplary aspect of the present invention, a reticle can be designed specifically to pattern structures with known line edge roughness values onto a wafer.

A metrology device can thereafter be employed to obtain measurements of line edge roughness from the structure(s) with known line edge roughness values. The metrology device can employ scanning electron microscopy techniques, scatterometry techniques, and/or other suitable techniques that can be employed to measure line edge roughness (e.g., electronic techniques to measure line edge roughness). Thereafter, a correcting component can generate an inverse function based upon a comparison between the measured line edge roughness values and the stored (known) line edge roughness values that correspond to the measured values. Thus, applying the inverse function to the measured values would result in output of the known values.

The metrology device can then obtain line edge roughness measurements upon structures that do not have known line edge roughness values. These obtained line edge roughness measurements are then subject to the inverse function, which modifies the line edge roughness values accordingly. Thus, the present invention enables obtainment of line edge roughness values that are independent of proprietary algorithms that are employed by metrology devices. Furthermore, manufacturing processes can be controlled based upon corrected line edge roughness values, as they are not tainted by proprietary algorithms. Thus, for instance, line edge roughness lying outside design specifications can be found and corrected based upon the corrected values.

To the accomplishment of the foregoing and related ends, the invention comprises the features hereinafter fully described and particularly pointed out in the claims. The following description and the annexed drawings set forth in detail certain illustrative aspects and implementations of the invention. These are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION

Figure 1:
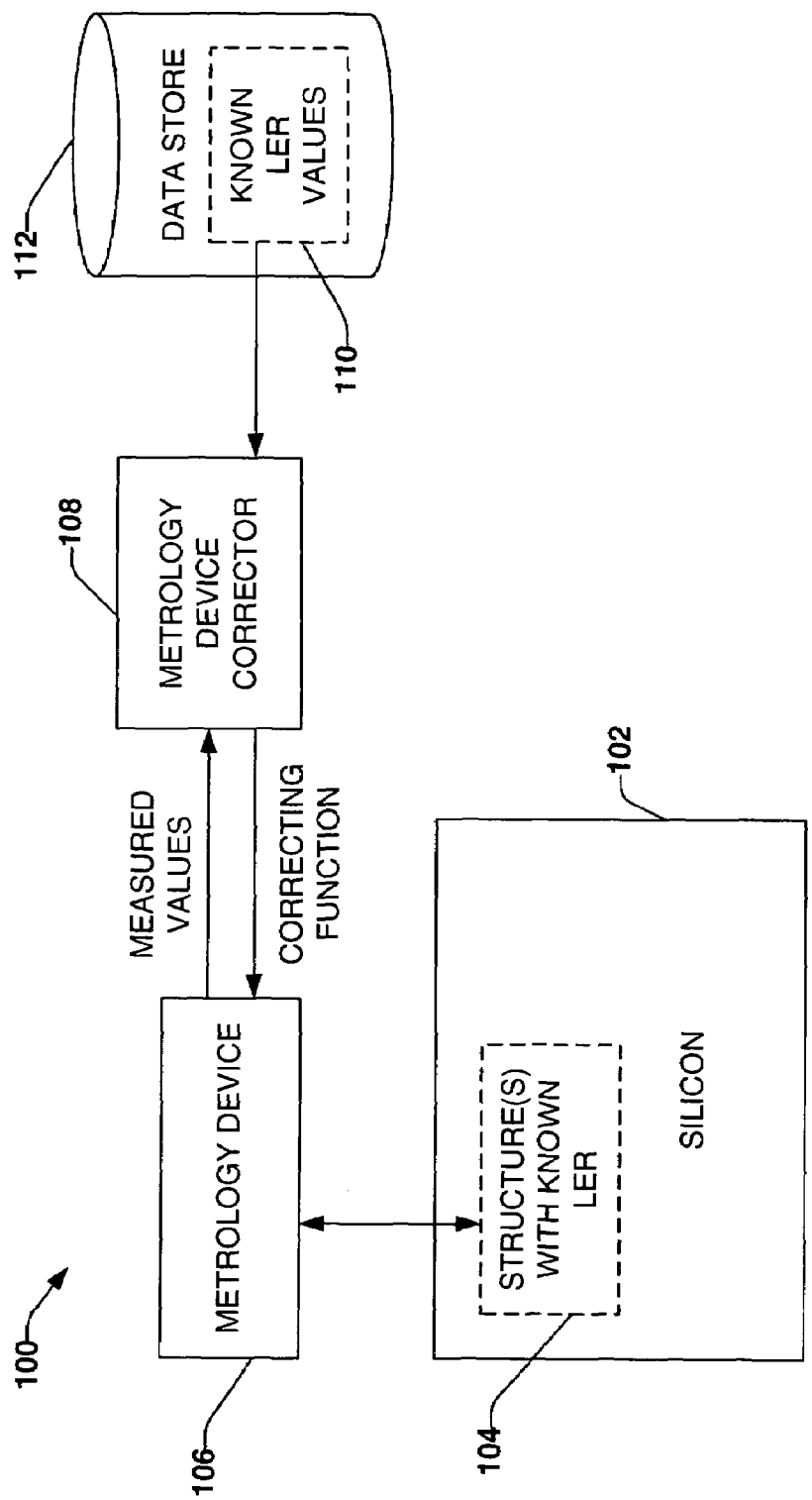
FIG. 1 is a block diagram of a system that facilitates obtainment of line edge roughness values that are independent of proprietorship of a metrology device in accordance with an aspect of the present invention.

The present invention is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As used in this application, the terms "component," "handler," "model," "system," and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers. Also, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal).

Referring first to FIG. 1, a system 100 that facilitates measurement of line-edge roughness (LER) independent of proprietorship of a metrology device is illustrated. The system 100 includes a portion of silicon 102 that contains a structure(s) with known LER 104. For example the structure(s) with known LER 104 can be placed upon the silicon 102 via a reticle mask and lithography techniques. In accordance with one aspect of the present invention, the structure(s) with known LER 104 can include particular LER patterns. For instance, the structure(s) with known LER 104 can include a square wave LER structure with a particular pitch, a rectangular wave LER structure with a particular pitch, and/or a sawtooth LER structure with a particular pitch. Furthermore, the structure with known LER can include reliability structures with embedded LER (e.g., a serpentine reliability structure, comb reliability structure, . . . ). Thus, it is understood that the structure(s) with known LER 104 can include any suitable structure with a known embedded line-edge roughness therein.

A metrology device 106 obtains measurements of LER from the structure(s) with known LER 104. For example, if the structure(s) with known LER 104 include a square wave LER structure and a sawtooth LER structure, the metrology device 104 can obtain measurements relating to both structures. The metrology device 106 can obtain measurements from any suitable number of disparate structures with a known embedded LER, and the previous example is not meant to limit such measurements to two LER structures. The metrology device 106 can employ scanning electron microscopy techniques (SEM) and/or scatterometry technology to measure LER upon the structure(s) with known LER 104, as well as electrically measure LER (e.g., by delivering current into a reliability test structure).

A metrology device corrector 108 receives LER results measured by the metrology device 106. The metrology device corrector 108 also receives known LER values 110 that reside within a data store 112. For example, these known LER values 110 can correspond to pitches in square LER structures, rectangular LER structures, sawtooth LER structures, etc. Furthermore, the known LER values can include information relating to amplitude, position of the structures, and any other suitable information that can be determined when measuring such structures. For example, these known LER values 110 can be employed in a program that is utilized to generate a reticle for the structure(s) with known LER 104. In accordance with another aspect of the present invention, the known LER values 110 can be determined from a trusted metrology tool (e.g., a metrology tool that is employed as a standard). Measuring the structure(s) with known LER 104 with a metrology tool employed as a standard as well as the metrology device 106 does not, however, enable in-line characterization and/or correction of the metrology device 106. For example, the structure(s) with known LER 104 must first be measured by the metrology tool utilized as the standard and thereafter measured by the metrology device 106. If LER values are programmed and embedded into a reticle, characterization of the metrology device 106 can occur in-line (e.g., without delay of requiring two disparate metrology tools to measure a LER structure).

The metrology device corrector 108 utilizes the measured results from the metrology device 106 and the known LER values 110 from within the data store 112 to generate a correcting function (e.g., an inverse function), wherein future LER measurements retrieved by the metrology device 106 will be subject to the correcting function. For example, the known LER values 110 can include values R1, R2, R3, and R4 that relate to LER values upon the structure(s) with known LER 104. The metrology device 106 can measure LER on the structure(s) with known LER, resulting in obtainment of values R1', R2', R3', and R4', where such values correspond to R1, R2, R3, and R4. The metrology device corrector 108 can utilize these values to generate a correcting function that is employable by the metrology device 106. Particularly, the metrology device 106 can utilize the correcting function to obtain accurate LER measurements from structures with unknown LER. Thus, the system 100 can provide in-line LER characterization while mitigating problems caused by a proprietary nature of conventional metrology devices.

Figure 2:
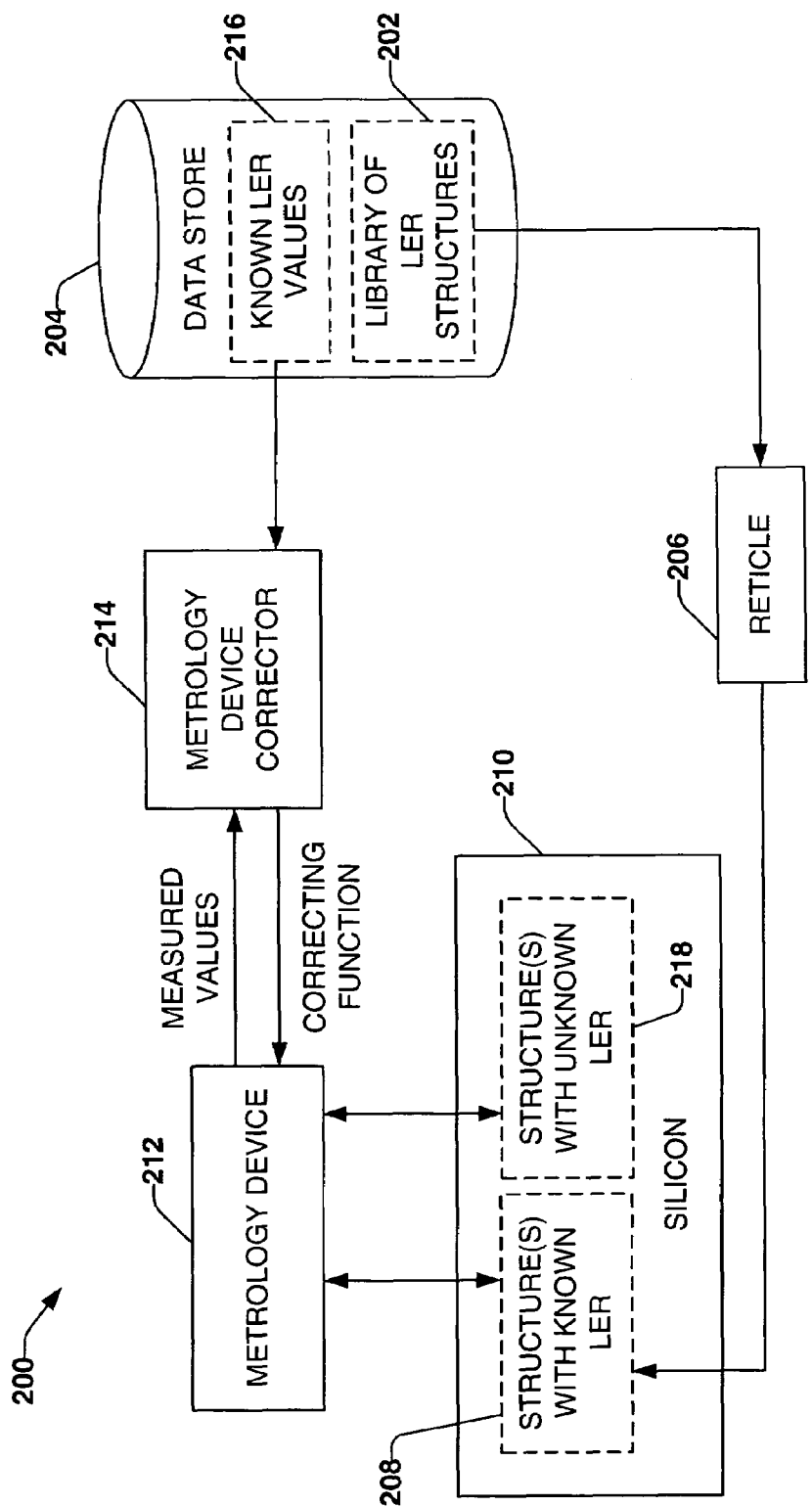
FIG. 2 is a block diagram of a system that facilitates obtainment of line edge roughness values that are independent of proprietorship of a metrology device in accordance with an aspect of the present invention.

Now referring to FIG. 2, a system 200 that facilitates extraction of tool-independent LER measurements from a structure with unknown LER is illustrated. The system 200 includes a library of LER structures 202 within a data store 204. The library of LER structures can include any suitable structure with a known embedded LER. For example, a rectangular wave structure with a particular amplitude and pitch can be a structure within the library of LER structures 202. Similarly, a square wave structure and a sawtooth structure with particular amplitude and pitch can be included within the library of LER structures 202, as well as reliability structures (e.g., comb/serpentine structures). One or more of the LER structures within the library of LER structures 202 can be placed on a reticle 206 and patterned onto a portion of silicon 208. This patterning creates structure(s) with known LER 210 on the silicon 208. Thus, it is to be understood that the structure(s) with known LER 208 correspond to one or more structure(s) within the library of structures 202.

A metrology device 212 is employed to measure LER on the structure(s) with known LER 208. Typically, the metrology device 212 employs proprietary metrology algorithms, resulting in disparate LER measurements when utilizing differing metrology devices. The metrology device 212 can obtain values for any suitable measurement of LER upon the structure(s) with known LER 208. For example, the metrology device 212 can obtain values for pitch and amplitude of a square wave structure, rectangular wave structure, and sawtooth structure. Additionally, in an instance that the structure(s) with known LER 208 include a reliability structure, the metrology device 212 can obtain electrical values by applying current to structures such as serpentine or comb structures, wherein such values are indicative of LER upon the reliability structures. Moreover, the metrology device 212 can employ any suitable technology for obtaining LER measurements. For instance, scatterometry techniques can be employed to obtain LER measurements from the structure(s) with known LER 208. Also, scanning electron microscope(s) can be utilized in connection with obtaining values of LER of the structure(s) with known LER 208.

LER values measured by the metrology device 212 are received by a metrology device corrector, which utilizes known LER values 216 within the data store 204 to generate a correcting function that will be employed by the metrology device 212. Specifically, the known LER values 216 correspond to the structure(s) with known LER 208 (e.g., the known LER values 216 relate to the library of LER structures 202 which are patterned onto the silicon 208 via the reticle 206). Thus, for example, values of LER measured by the metrology device 212 are compared with known LER values 216 by the metrology device corrector 214, and a correcting function is generated based at least in part upon the comparison. For example, the correcting function can result in a cubic equation, a quadratic equation, or any other suitable equation that can be utilized as a correcting function.

Upon generation of the correcting function by the metrology device corrector 214, the metrology device 212 can measure LER on structure(s) 218 that are not associated with pre-determined LER values. These structure(s) 218 with unknown LER can be patterned by the reticle 206 or a disparate reticle (not shown), such as during instances that the reticle 206 is specially designed to generate the structure(s) with known LER 208. The correcting function can be applied to these measured values, thereby obtaining LER values that are independent of proprietorship of the metrology device 212. The system 200 enables extraction of LER values that are independent of a metrology device proprietor in-line (e.g., during manufacturing of an integrated circuit). These corrected LER values can thereafter be utilized for more efficient control of an integrated circuit manufacturing process. For example, rather than designing several controllers relating to disparate metrology devices, a single controller can be designed and employed relating to each metrology device. Furthermore, etching processes can be monitored and controlled based at least in part upon the corrected LER values, and reticle(s) utilized to create patterns on the silicon can be monitored for defects.

Figure 3:
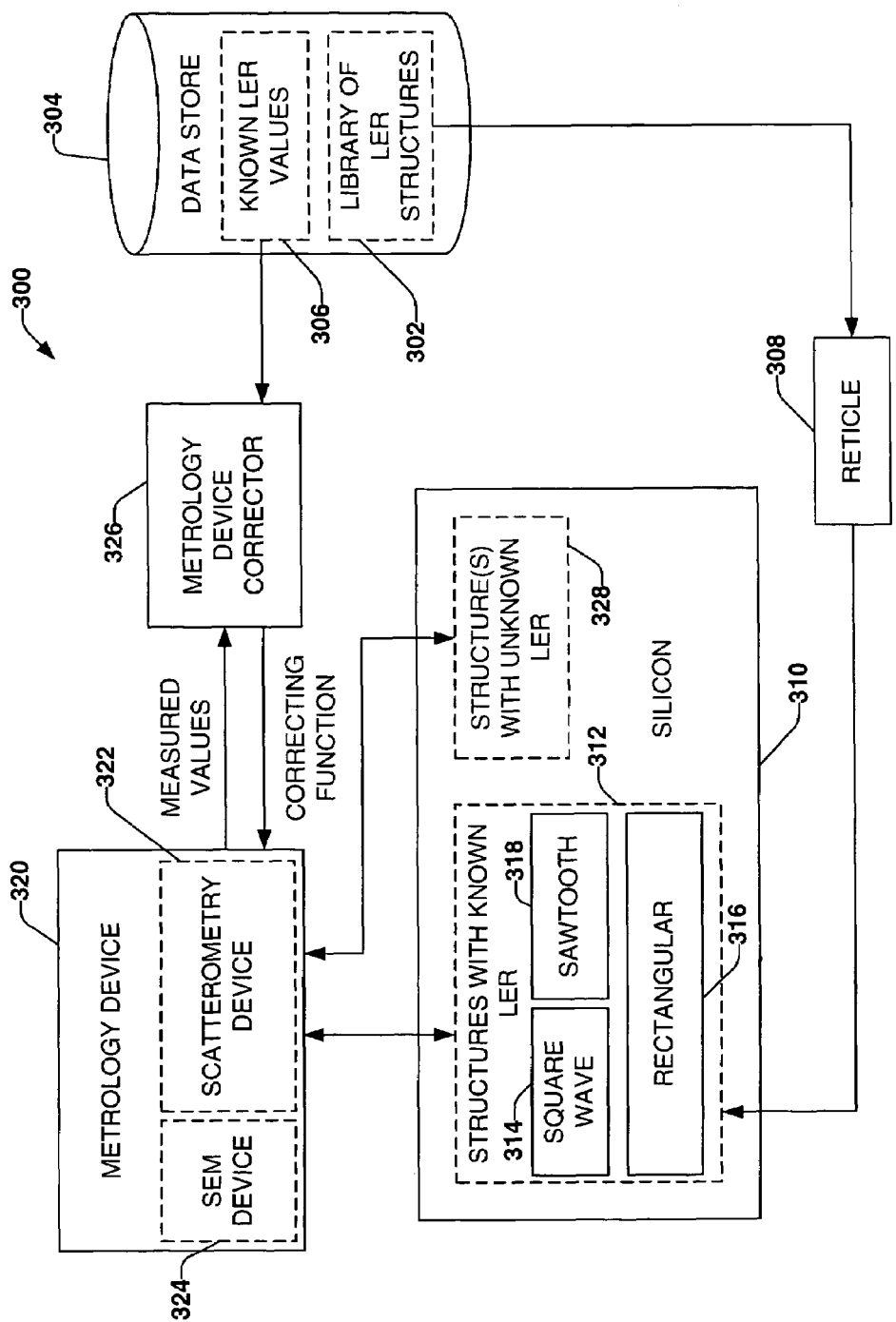
FIG. 3 is a block diagram of a system that facilitates obtainment of line edge roughness values that are independent of proprietorship of a metrology device in accordance with an aspect of the present invention.

Turning now to FIG. 3, a system 300 that facilitates extraction of LER values independent of proprietorship of a metrology device is illustrated. The system 300 includes a library of LER structures 302 within a data store 304, wherein the LER structures within the library of LER structures 302 are associated with known LER values 306. A plurality of structures within the library of LER structures 302 are placed upon a reticle 308, which is utilized to pattern the plurality of structures within the library of structures 302 onto silicon 310, thereby creating structures with known LER 312. These structures with known LER 312 include a square wave LER structure 312, a rectangular wave LER structure 316, and a sawtooth wave LER structure 318. As discussed previously, these LER structures 314, 316, and 318 correspond to one or more structures within the library of structures 302, and have known LER values 306 associated therewith.

A metrology device 320 is employed to measure one or more values relating to LER of the LER structures 314, 316, and 318. For example, the metrology device 320 can obtain measurements relating to pitch and/or amplitude of the square wave structure 314, rectangular wave structure 316, and sawtooth wave structure 318. While pitch and amplitude are two exemplary values that can be measured, it is understood that any suitable values relating to LER can be obtained by the metrology device 320. The metrology device 320 can employ a scatterometry device 320 to obtain measurements related to LER. Particularly, light can be delivered to the structures with known LER 312, and light reflected/refracted therefrom can be captured and analyzed to determine one or more LER measurements. Furthermore, the metrology device 320 can employ a SEM device 324 to obtain measurements relating to LER from the structures with known LER 312. While the metrology device 320 is illustrated as containing both a scatterometry device 322 and a SEM device 324, it is understood that the metrology device 320 can include only one of such devices. Furthermore, the metrology device 320 can employ any suitable technology for obtaining measurements relating to LER of the structures 314, 316, and 318.

A metrology device corrector 326 receives values of LER relating to the structures with known LER 312 from the metrology device 320. The metrology device corrector 326 also receives the known LER values 306 from the data store 304, and generates a function that corrects LER values measured by the metrology device 320 based upon the measured values of LER and the known LER values 306. Particularly, the metrology device 320 can obtain a plurality of LER measurements from the structures 314, 316, and 318 and relay such values to the metrology device corrector 326. The metrology device corrector 326 can retrieve a plurality of known LER values 306 corresponding to the measured values and generate a correcting function based at least in part upon differences between the measured values and known values 306.

Thereafter, the metrology device 320 can be employed to obtain measurements relating to LER upon integrated circuit structure(s) 328 with unknown LER. These obtained values can thereafter be modified by the correcting function, resulting in LER measurements that are independent of proprietorship of the metrology device 320.

Figure 4:
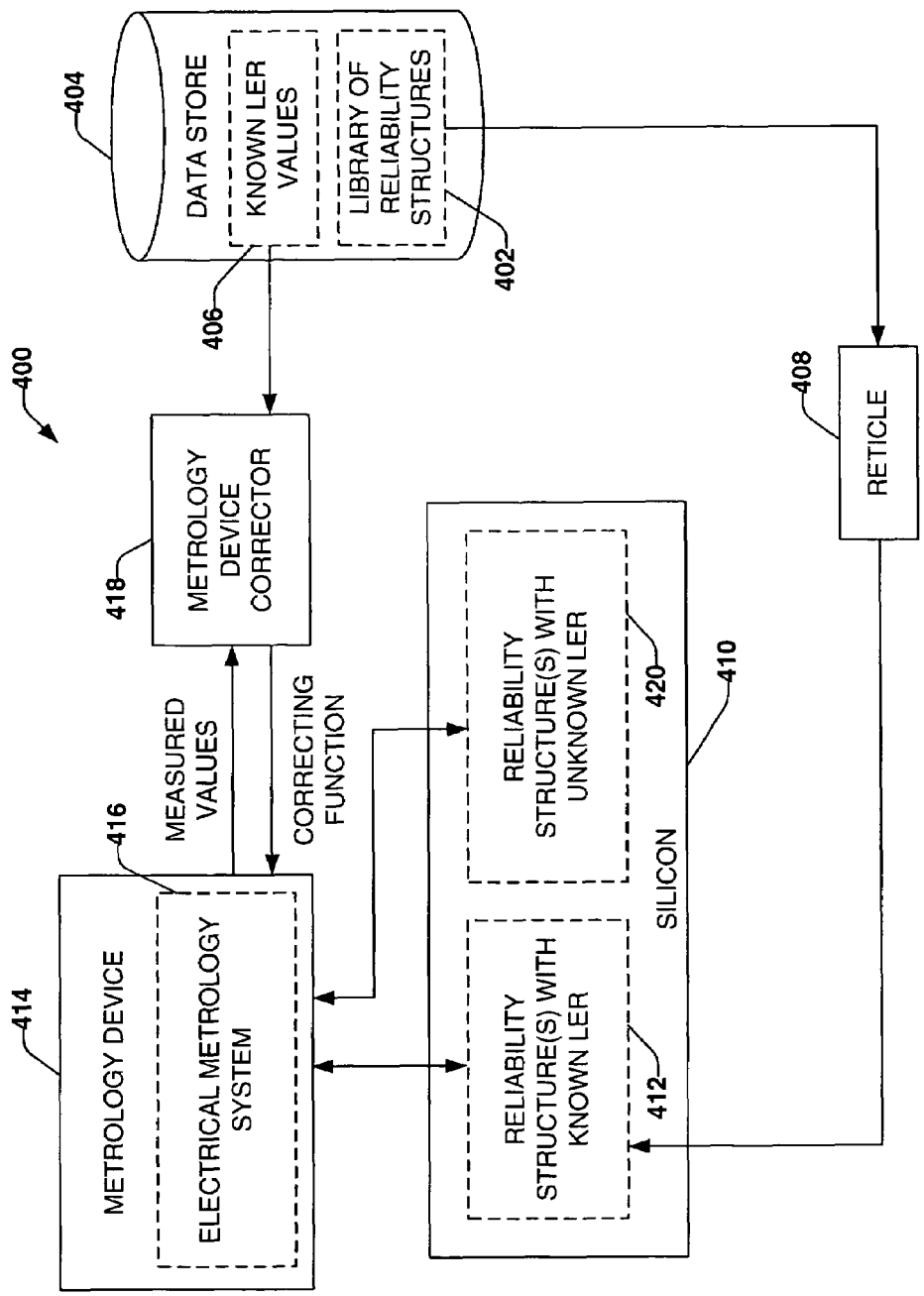
FIG. 4 is a block diagram of a system that facilitates obtainment of line edge roughness values that are independent of proprietorship of a metrology device in accordance with an aspect of the present invention.

Now referring to FIG. 4, a system 400 that facilitates in-line electrical measurement of LER via utilizing reliability structures is illustrated. The system 400 includes a library of reliability structures 402 within a data store 404, wherein the library of reliability structures 402 is associated with known LER values 406. While the library of reliability structures 402 and the known LER values 406 are shown to reside in a single data store, the known LER values 406 and the library of reliability structures 402 associated therewith can reside in disparate data stores.

The library of reliability structures 402 are placed onto a reticle 408 and subsequently patterned onto silicon 410, resulting in generation of reliability structure(s) with known LER 412 on the silicon 410. For example, these reliability structures can be comb structures, serpentine structures, or the like. A metrology device 414 is employed to measure LER resident upon the reliability structures 412. For example, the metrology device 414 can employ an electrical metrology system 416 to obtain LER measurements from the reliability structures with known LER 412. For instance, a particular current value can be delivered over at least a portion of the reliability structure(s) with known LER 412, and output current can be analyzed to determine values of LER resident thereon. The measured values are relayed to a metrology device corrector 418, which also retrieves the known LER values 406 corresponding thereto. Based upon a comparison between the known LER values 406 and measured values obtained by the metrology device 414, a correcting function can be generated that operates to render the metrology device 414 independent of its proprietor.

Thereafter, the metrology device 414 can obtain measurements of LER relating to reliability structure(s) with unknown LER 420. Such obtained measurements are then subject to the correcting function generated by the metrology device corrector 418. Furthermore, the metrology device 414 can measure disparate structures that are not utilized as reliability structures (e.g., the metrology device 414 can obtain LER measurements from any suitable integrated circuit structure). Thereafter, these measurements can be modified via the correcting function rendering LER measurements independent of proprietorship of the metrology device 414.

Figure 5:
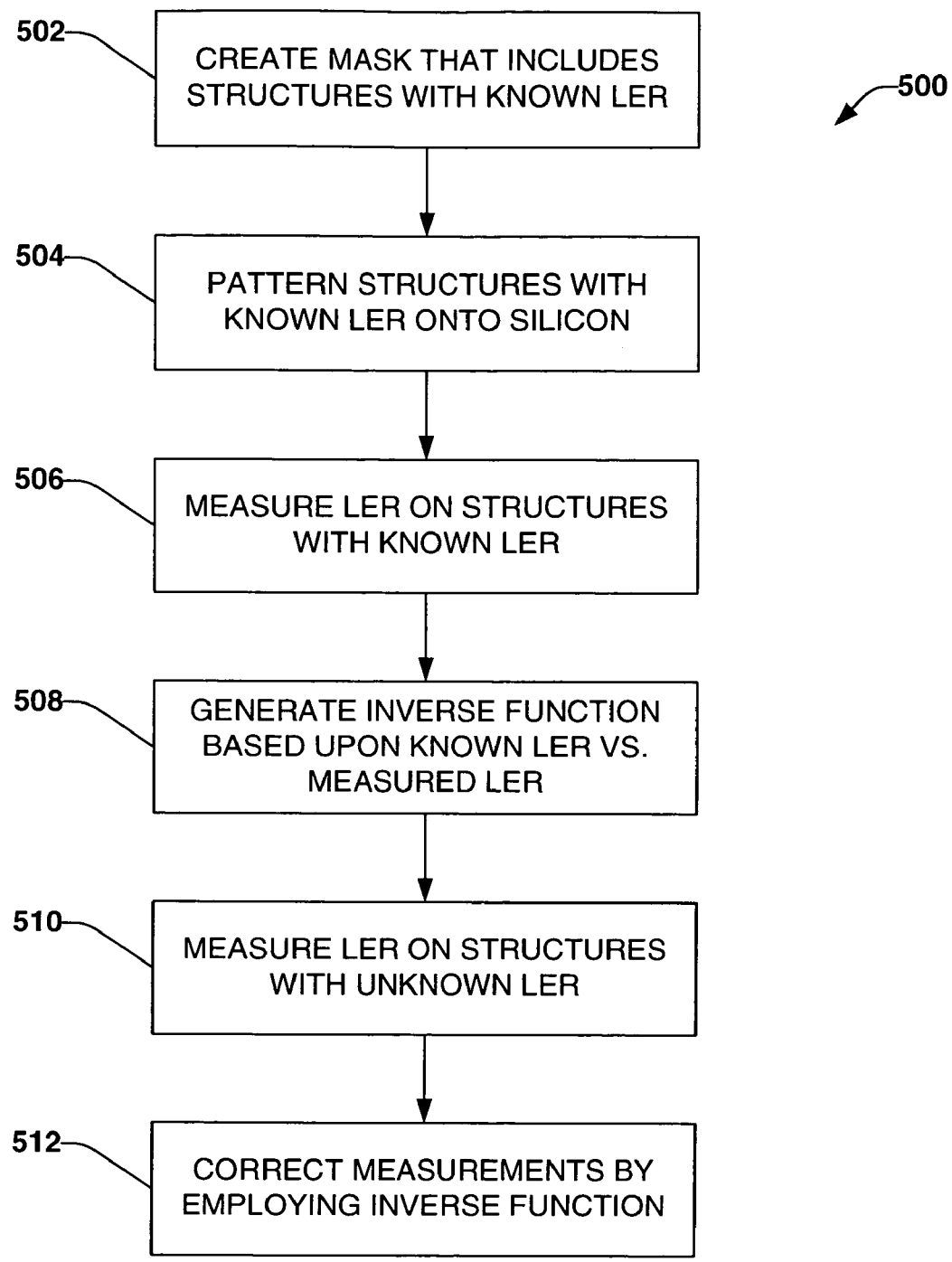
FIG. 5 is a flow diagram that illustrates a methodology for obtaining metrology device independent line edge roughness measurements in accordance with an aspect of the present invention.

Referring now to FIG. 5, a methodology 500 for obtaining LER measurements independent of a proprietor of a metrology device is illustrated. While, for purposes of simplicity of explanation, the methodology 500 is shown and described as a series of acts, it is to be understood and appreciated that the present invention is not limited by the order of acts, as some acts may, in accordance with the present invention, occur in different orders and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the present invention.

At 502, a reticle is created, wherein such reticle includes patterns and/or structures with known LER. For example, a structure with a square wave pattern embedded therein can be placed on the reticle. Furthermore, structures with sawtooth wave patterns and/or rectangular wave patterns as well as any other suitable LER pattern can be placed onto the created reticle. In accordance with one aspect of the present invention, the generated reticle is created specifically to contain only structures with known LER. In such an embodiment, a disparate reticle can be employed to pattern an integrated circuit and stepped over a wafer until exposure is completed. This allows for less space to be consumed by the structures with known LER on the wafer, thereby maximizing utilization of wafer space for integrated circuit components. Alternatively, the known LER structures can be embedded within a reticle together with a plurality of integrated circuit components. Measurements relating to the structures can be known and stored in a data store. For instance, pitch of a square wave, rectangular wave, and/or a sawtooth wave can be known and stored within a data store. Similarly, various other values relating to LER can be stored for later usage.

At 504, the structures with known LER on the reticle are patterned onto silicon (e.g., a portion of a wafer). Conventional lithography techniques can be employed to pattern such structures with known LER on the silicon. Furthermore, various other patterning techniques, such as immersion lithography, can be employed in connection with patterning structures with known embedded LER onto the silicon.

At 506, a metrology device is employed to obtain measurements of LER values from the structures with known LER. For example, the metrology device can obtain measurements relating to a pitch of a wave, amplitude of a wave, wavelength, or any other suitable measurement relating to LER that can be obtained. For instance, a scanning electron microscope can be utilized in connection with obtaining values of LER. Furthermore, scatterometry techniques as well as electrical measuring/monitoring techniques can be employed in connection with obtaining values of LER via a metrology device.

At 508, an inverse function (e.g., a correcting function) is generated based at least in part upon a comparison between the known LER values and the LER values obtained from the metrology device. For a particular example, the known LER values relating to the structures on the reticle can be R1, R2, R3, and R4, while the LER values obtained from the metrology device are R1', R2', R3', and R4'. An inverse function is generated which effectively transforms the measured values R1', R2', R3', and R4' to the known values R1, R2, R3, and R4 when applied to such measured values. While four measurements are given as an example, it is understood that any suitable number of measurements can be employed in connection with generating an inverse function.

At 510, structures with unknown LER are measured. For instance, it may be desirable to obtain LER measurements to facilitate accurate and efficient control of a manufacturing process (e.g., etching, lithography, . . . ). These measurements are obtained by the metrology device through any suitable means. For example, scatterometry and SEM techniques can be employed to obtain measurements relating to LER on integrated circuit structures. At 512, the inverse function is employed to correct the obtained measurements, thereby providing LER values that are independent of proprietorship of the metrology device. The corrected measurements can be displayed to a user and/or utilized in connection with correcting LER that falls outside of design specifications. Furthermore, the corrected measurements can be employed with confidence in connection with controlling semiconductor manufacturing process(es) that are impacted by LER upon structures.

Figure 6:
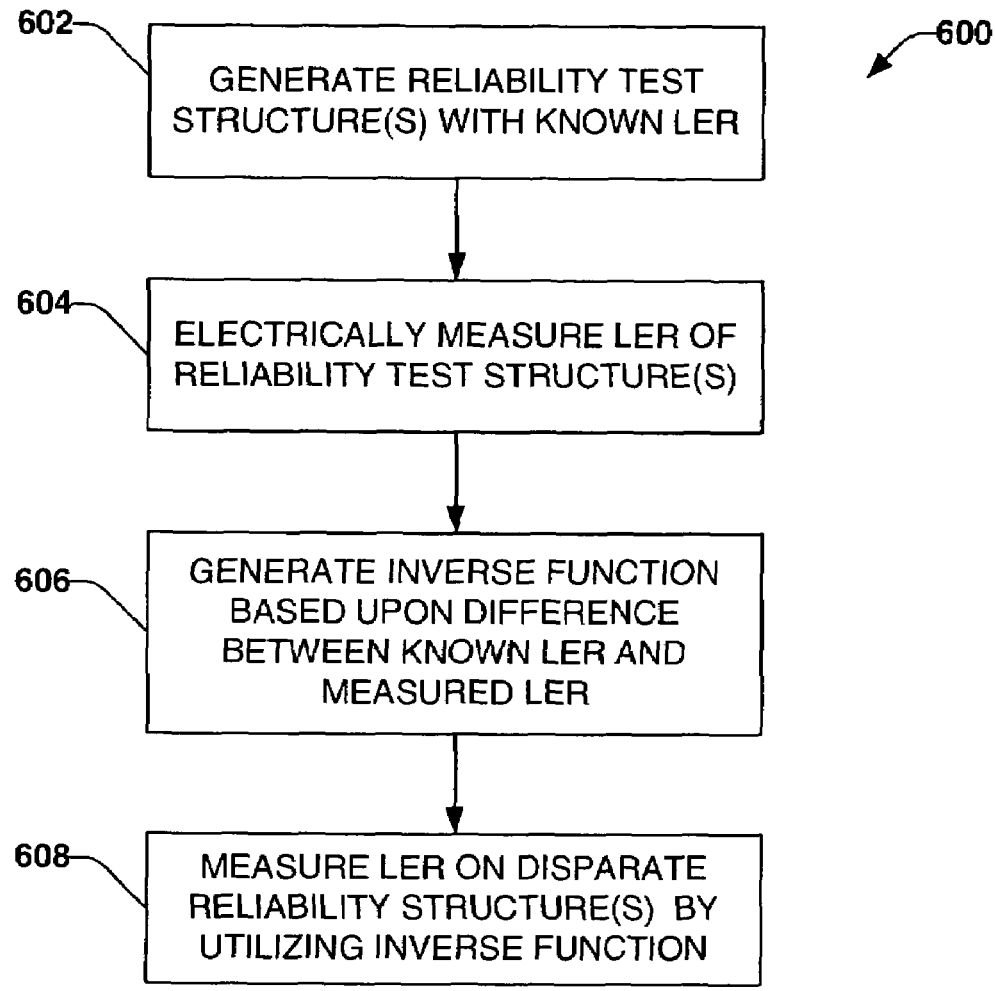
FIG. 6 is a flow diagram that illustrates a methodology for obtaining metrology device independent line edge roughness measurements in accordance with an aspect of the present invention.

Now referring to FIG. 6, a methodology 600 that facilitates extraction of metrology device independent LER values is illustrated. At 602, reliability test structure(s) with known LER are generated upon silicon (e.g., a wafer). For example, lithography, immersion lithography, or any other suitable patterning can be employed in connection with the present invention. Furthermore, the silicon can be etched (e.g., wet or dry etching can be employed) to generate these reliability structures with a known LER embedded therein. For instance, particular LER patterns can be embedded within the reliability structures. The reliability structures can be, for example, serpentine structures and/or comb structures and the like.

At 604, LER upon the reliability structures are measured electrically. For example, particular currents can be delivered through the reliability test structures, and these currents can be monitored at different portions of the reliability test structures to obtain LER values. Alternatively, SEM and/or scatterometry techniques can be employed to obtain LER values from the reliability structures.

At 606 an inverse function is generated based at least in part upon comparison of the obtained measured values of LER and the known values of LER. Thus, subjecting the measured values of LER to the inverse function will result in an output of the known values of LER. At 608, LER is measured upon disparate reliability structures via employing the metrology techniques and the inverse function. For example, measured values of LER upon the structures are subject to the inverse function, which modifies such values according to previous differences between known values of LER and measured values of LER. Thus, the methodology 600 enables extraction of LER values independent of proprietorship of the metrology device and/or method.

Figure 7:
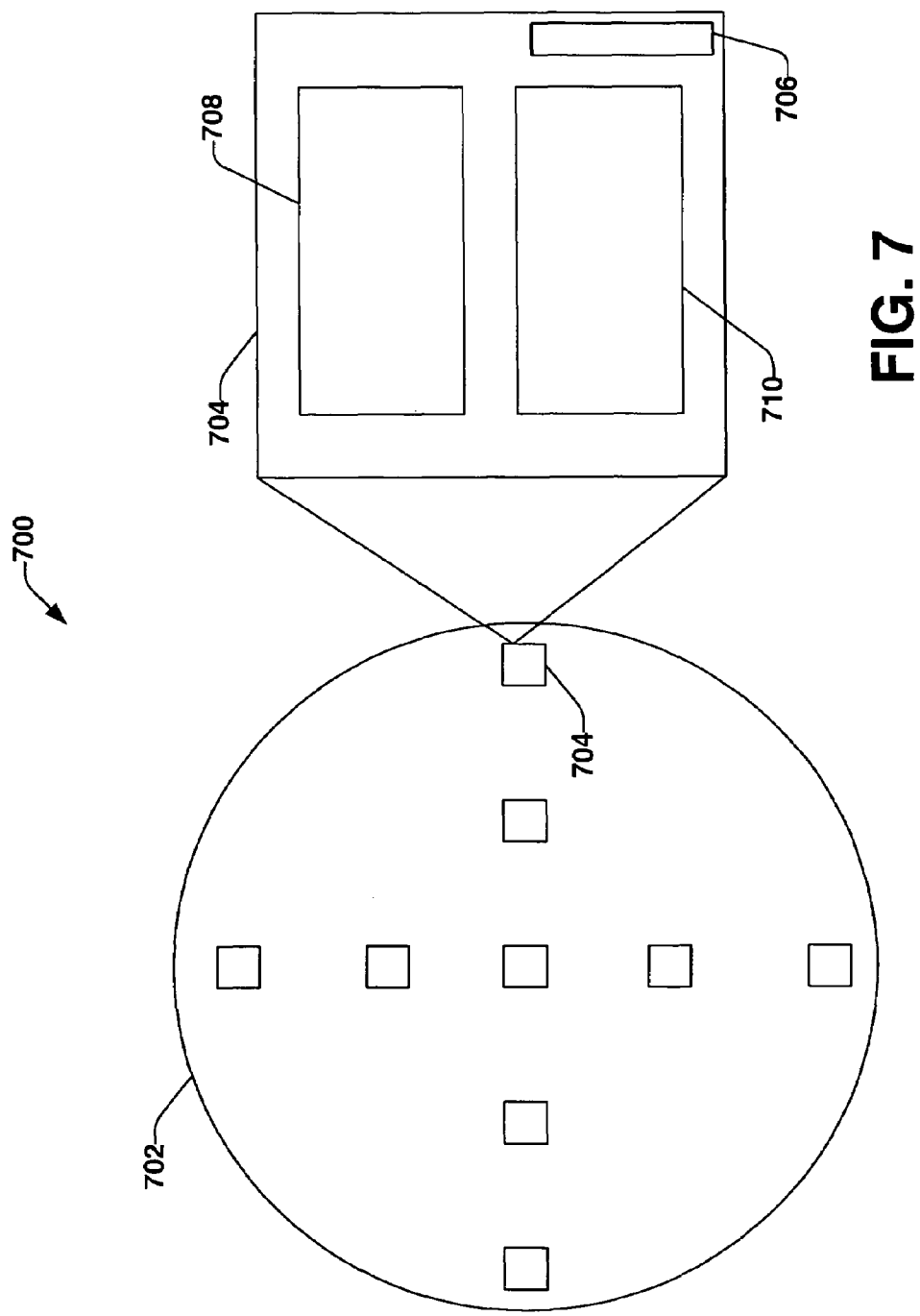
FIG. 7 illustrates an exemplary embodiment that can be employed in connection with the present invention.

Now turning to FIG. 7, an exemplary embodiment 700 of the present invention is illustrated. A wafer 702 is shown with a plurality of segments 704 that are designed to facilitate in-line extraction of LER measurements that are independent of proprietorship of a metrology device utilized to obtain these measurements. Particularly, the segments 704 include one or more programmed LER structures 706 that have known LER embedded therein. For example, a square wave structure, a rectangular wave structure, a sawtooth structure, a reliability structure, or a combination thereof can be included within the programmed LER structures 706.

A metrology device (not shown) can be employed to obtain measurements related to the programmed LER structures. For instance, wavelength, pitch of a wave, amplitude, and any other suitable measurement relating to LER can be obtained by a metrology device. These measurements can then be compared with corresponding known values of LER relating to the structures 706. Particularly, the programmed structures 706 can be employed to de-convolve tool-specific metrology algorithms by generating an inverse function by comparing measured values with corresponding known values. Thus, an inverse function is generated that enables extraction of metrology device independent LER values.

The segments 704 can also include integrated circuit structures 708, 710 that are associated with LER that can be measured by a metrology device but whose measurements are unknown. The metrology device that is associated with the inverse function can obtain measurements of LER for the structures 708 and 710, which can thereafter be relayed to the inverse function to obtain LER values independent of the metrology tool proprietor. Furthermore, each wafer is not required to include one or more segments that contain programmed LER structures. For example, if space on the wafer 702 is at a premium, an inverse function can be generated prior to patterning the wafer 702. However, providing one or more segments that include programmed LER structures on a wafer allows for in-line monitoring and correction of metrology devices.

Figure 8:
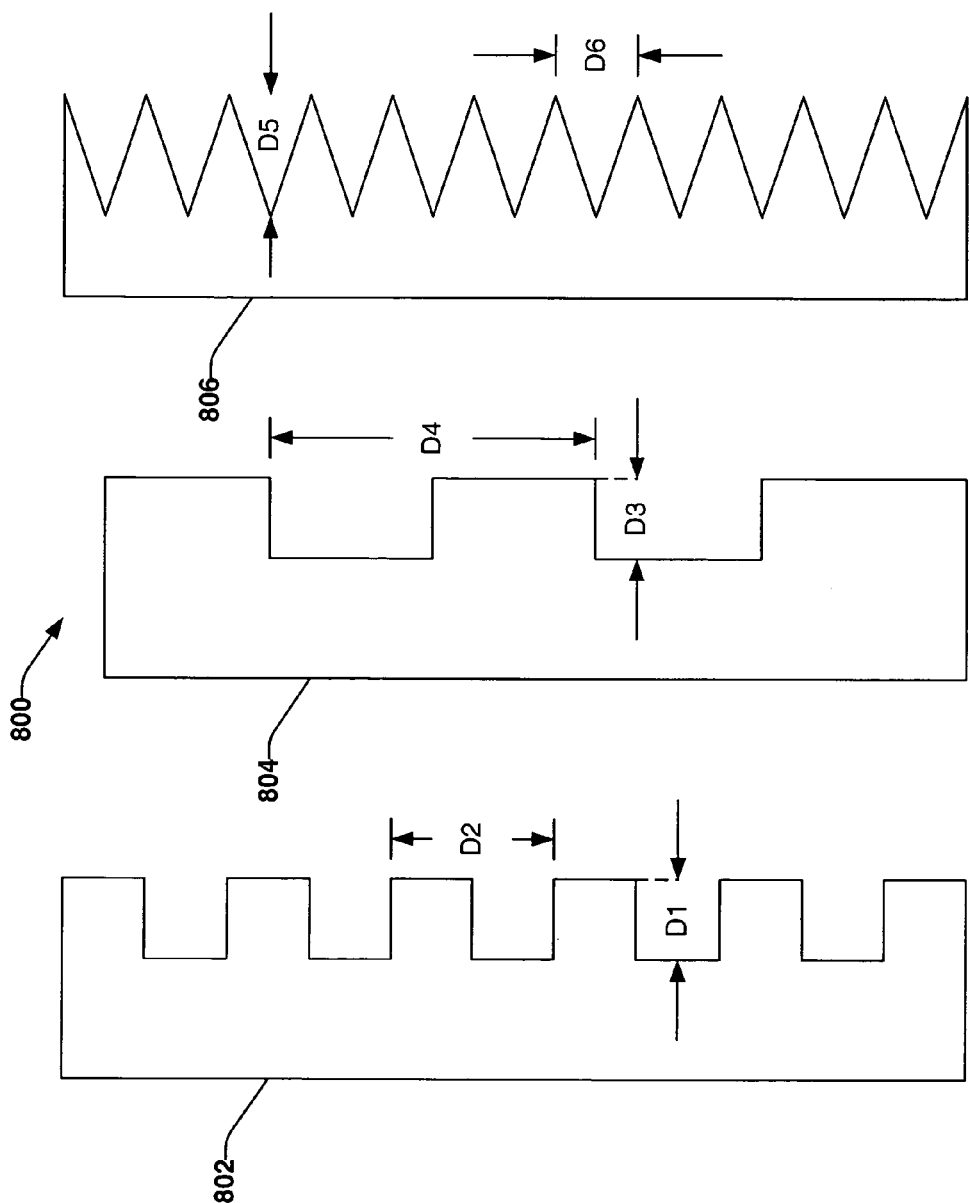
FIG. 8 illustrates exemplary structures with known line edge roughness values that can be employed in connection with the present invention.

Referring now to FIG. 8, a plurality of structures 800 with known embedded LER values is illustrated. A square wave structure 802 is illustrated with a particular known amplitude D1 and wavelength D2. Furthermore, while not shown, the square wave structure 802 can have a known pitch. Similarly, a rectangular wave structure 804 can have a known amplitude D3 and a known wavelength D4 as well as a particular pitch, and a sawtooth wave structure 806 can have a known amplitude D5 and wavelength D6 (and thus a known pitch). These structures and their known values can be employed to de-convolve metrology algorithms in order to provide tool-independent LER measurements. While the square wave structure 802, rectangular wave structure 804, and sawtooth wave structure 806 are presented as exemplary programmed LER structures, it is understood that any suitable structures with known LER values can be employed in connection with the present invention.

Figure 9:
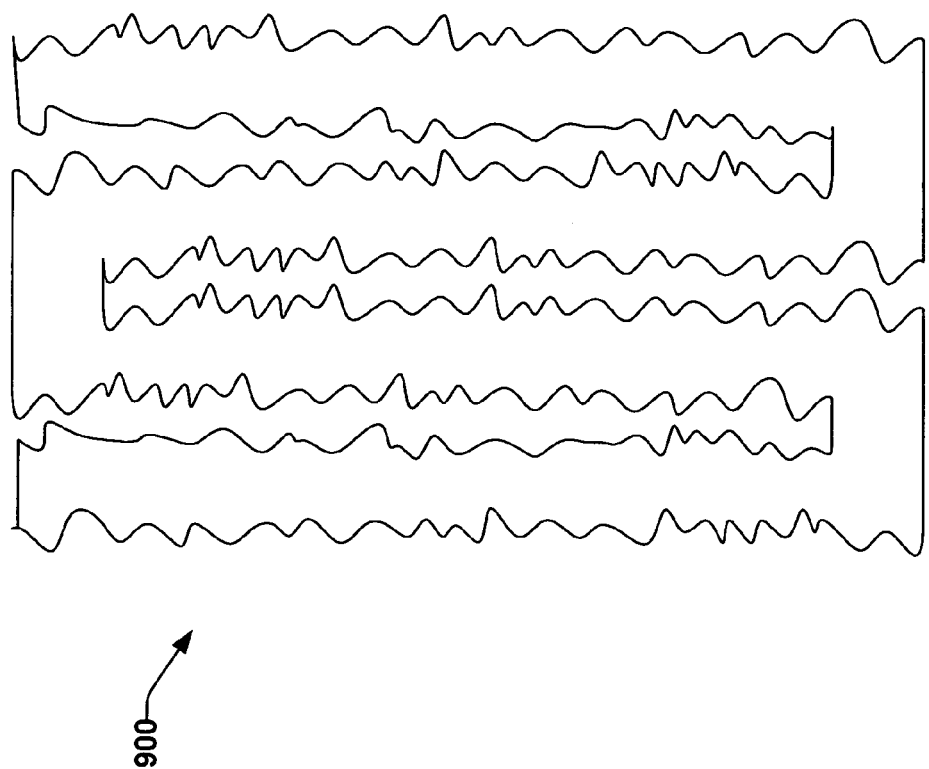
FIG. 9 is an exemplary reliability structure that can be employed in connection with the present invention.

Turning now to FIG. 9, an exemplary reliability structure 900 with known embedded LER is illustrated. The reliability structure 900 is illustrated as a serpentine structure, but it is to be understood that any suitable reliability structure can be employed in connection with the present invention. The reliability structure 900 includes embedded LER that is known. While not illustrated in this exemplary structure 900, the walls of the reliability structure can include disparate LER waves. Thereafter, the LER can be electrically measured via known LER measurement methods. Similarly, a SEM tool and/or a scatterometry device can be employed in connection with measuring LER resident upon the reliability structure. Thereafter an inverse (correcting) function can be generated based on a comparison between the known LER values and the measured LER values. Structures with unknown LER can then be measured without those measurements being acquired by an algorithm specific to the metrology tool. Utilizing the present invention can create a uniform metrology standard, thereby enabling more efficient control of manufacturing processes that require monitoring and/or correction of LER.

Figure 10:
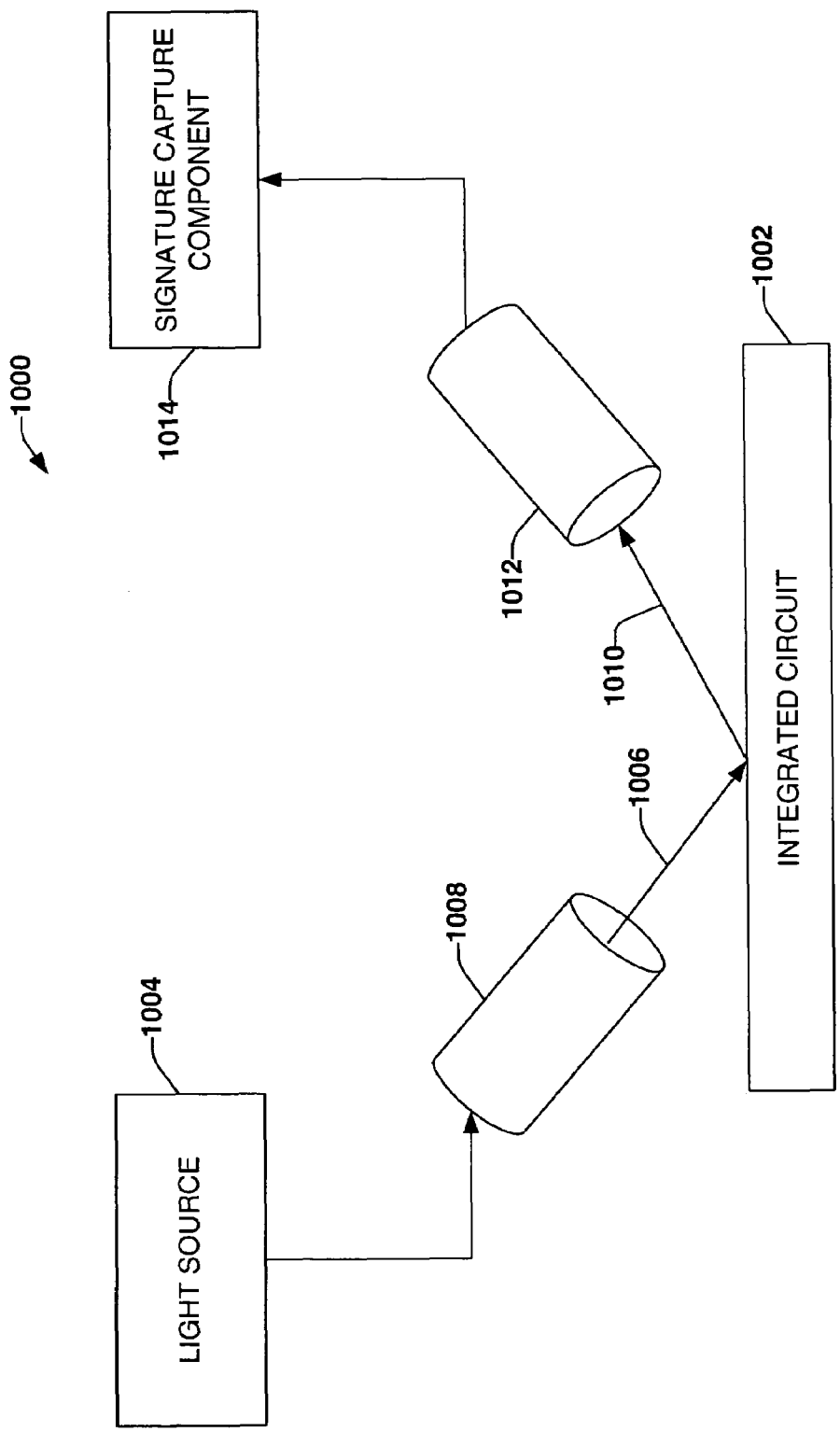
FIG. 10 illustrates an exemplary scatterometry system that can be employed in connection with the present invention.

Turning now to FIG. 10, one aspect of the present invention is shown. FIG. 10 illustrates a scatterometry system 1000 being employed to generate a signature of a routing pattern resident upon an integrated circuit 1002. A light source 1004 directs a light 1006 through a light-directing component 1008 incident to the surface of the integrated circuit 1002. Reflected light 1010 from the integrated circuit 1002 is captured by a light-detecting component 1012, which transmits the collected light and/or data associated with the collected light to a signature capture component 1014. The signature capture component 1014 can, for example, employ a processor (not shown) which receives the light 1008 collected by the light detecting component 1010 and generates a signature of one or more routing patterns based upon such reflected light. This signature can thereafter be compared with other signatures stored within a library of signatures to control routing upon the integrated circuit 1002.

Figure 11:
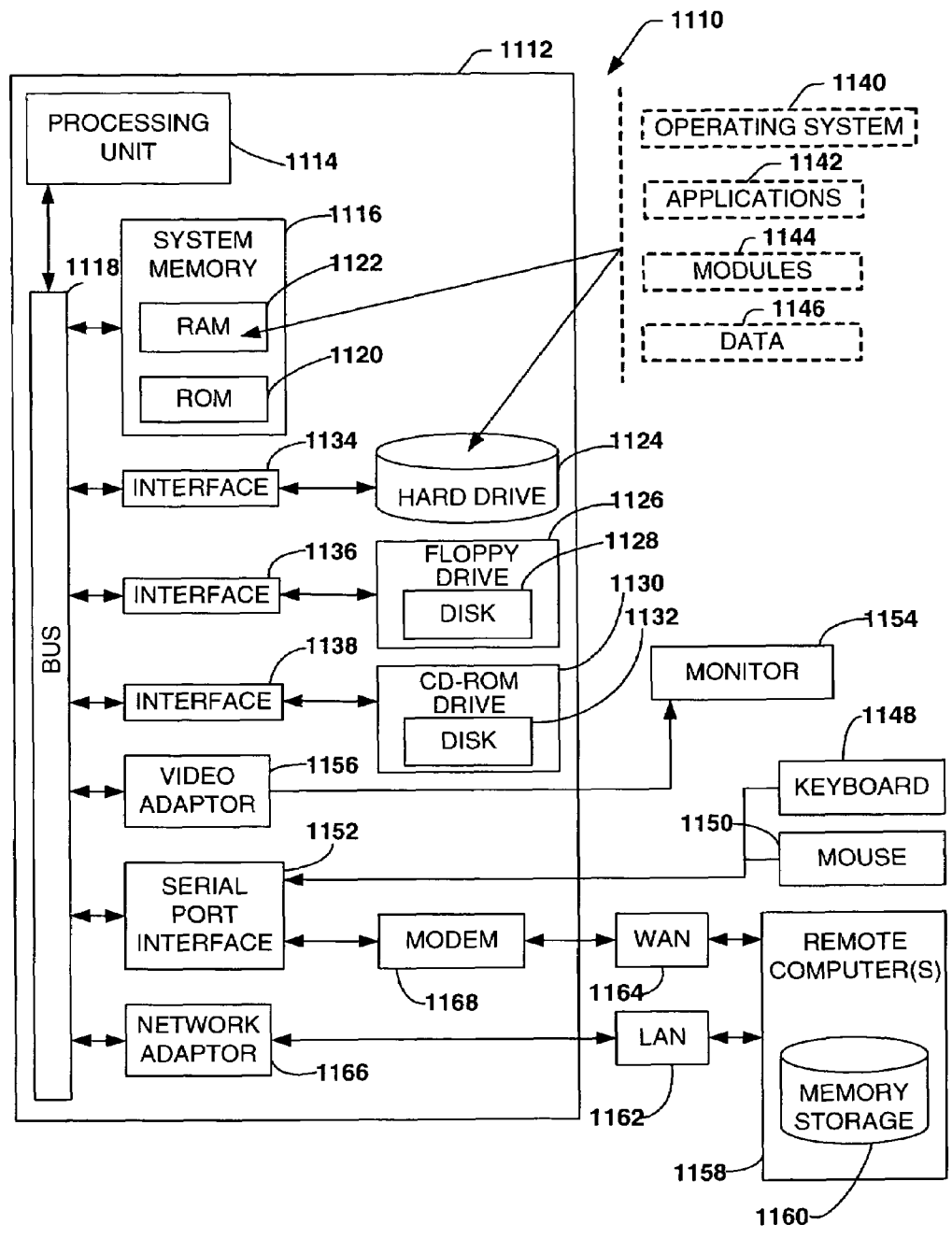
FIG. 11 is an exemplary computing environment that can be utilized in connection with the present invention.

In order to provide additional context for various aspects of the present invention, FIG. 11 and the following discussion are intended to provide a brief, general description of a suitable computing environment 1110 in which the various aspects of the present invention can be implemented. While the invention has been described above in the general context of computer-executable instructions that may run on one or more computers, those skilled in the art will recognize that the invention also may be implemented in combination with other program modules and/or as a combination of hardware and software. Generally, program modules include routines, programs, components, data structures, etc. that perform particular tasks or implement particular abstract data types. Moreover, those skilled in the art will appreciate that the inventive methods may be practiced with other computer system configurations, including single-processor or multiprocessor computer systems, minicomputers, mainframe computers, as well as personal computers, hand-held computing devices, microprocessor-based or programmable consumer electronics, and the like, each of which may be operatively coupled to one or more associated devices. The illustrated aspects of the invention may also be practiced in distributed computing environments where certain tasks are performed by remote processing devices that are linked through a communications network. In a distributed computing environment, program modules may be located in both local and remote memory storage devices.

With reference to FIG. 11, an exemplary environment 1110 for implementing various aspects of the invention includes a computer 1112, including a processing unit 1114, a system memory 1116, and a system bus 1118 that couples various system components including the system memory to the processing unit 1114. The processing unit 1114 may be any of various commercially available processors. Dual microprocessors and other multi-processor architectures also can be used as the processing unit 1114.

The system bus 1118 can be any of several types of bus structure including a memory bus or memory controller, a peripheral bus, and a local bus using any of a variety of conventional bus architectures such as PCI, VESA, Microchannel, ISA, and EISA, to name a few. The system memory 1116 includes read only memory (ROM) 1120 and random access memory (RAM) 1122. A basic input/output system (BIOS), containing the basic routines that help to transfer information between elements within the computer 1112, such as during start-up, is stored in ROM 1120.

The computer 1112 further includes a hard disk drive 1124, a magnetic disk drive 1126 to read from or write to, for example, a removable disk 1128, and an optical disk drive 1130 for reading, for example, from a CD-ROM disk 1132 or to read from or write to other optical media. The hard disk drive 1124, magnetic disk drive 1126, and optical disk drive 1130 are connected to the system bus 1118 by a hard disk drive interface 1134, a magnetic disk drive interface 1136, and an optical drive interface 1138, respectively. The drives and their associated computer-readable media provide nonvolatile storage of data, data structures, computer-executable instructions, etc. for the computer 1112, including for the storage of broadcast programming in a suitable digital format. Although the description of computer-readable media above refers to a hard disk, a removable magnetic disk and a CD, it should be appreciated by those skilled in the art that other types of media which are readable by a computer, such as magnetic cassettes, flash memory cards, digital video disks, Bernoulli cartridges, and the like, may also be used in the exemplary operating environment, and further that any such media may contain computer-executable instructions for performing the methods of the present invention.

A number of program modules may be stored in the drives and RAM 1122, including an operating system 1140, one or more application programs 1142, other program modules 1144, and program data 1146. The operating system 1140 in the illustrated computer is, for example, the "Microsoft® Windows® NT" operating system, although it is to be appreciated that the present invention may be implemented with other operating systems or combinations of operating systems, such as UNIX®, LINUX®, etc.

A user may enter commands and information into the computer 1112 through a keyboard 1148 and a pointing device, such as a mouse 1150. Other input devices (not shown) may include a microphone, an IR remote control, a joystick, a game pad, a satellite dish, a scanner, or the like. These and other input devices are often connected to the processing unit 1114 through a serial port interface 1152 that is coupled to the system bus 1118, but may be connected by other interfaces, such as a parallel port, a game port, a universal serial bus ("USB"), an IR interface, etc. A monitor 1154 or other type of display device is also connected to the system bus 1118 via an interface, such as a video adapter 1156. In addition to the monitor, a computer typically includes other peripheral output devices (not shown), such as speakers, printers etc.

The computer 1112 may operate in a networked environment using logical connections to one or more remote computers, such as a remote computer(s) 1158. The remote computer(s) 1158 may be a workstation, a server computer, a router, a personal computer, microprocessor based entertainment appliance (e.g., a WEBTV® client system), a peer device or other common network node, and typically includes many or all of the elements described relative to the computer 1112, although, for purposes of brevity, only a memory storage device 1160 is illustrated. The logical connections depicted include a local area network (LAN) 1162 and a wide area network (WAN) 1164. Such networking environments are commonplace in offices, enterprise-wide computer networks, intranets and the Internet.

When used in a LAN networking environment, the computer 1112 is connected to the local network 1162 through a network interface or adapter 1166. When used in a WAN networking environment, the computer 1112 typically includes a modem 1168, or is connected to a communications server on the LAN, or has other means for establishing communications over the WAN 1164, such as the Internet. The modem 1168, which may be internal or external, is connected to the system bus 1118 via the serial port interface 1152 to enable communications, for example, via POTS. The modem 1168 may also, in an alternative embodiment, be connected to the network adaptor 1166 to enable communications, for example, via DSL or cable. In a networked environment, program modules depicted relative to the computer 1112, or portions thereof, will be stored in the remote memory storage device 1160. It may be appreciated that the network connections shown are exemplary and other means of establishing a communications link between the computers may be used.

What has been described above is one or more aspects of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims. In addition, while a particular feature of the invention may have been disclosed with respect to only one of several implementations, such feature may be combined with one or more other features of the other implementations as may be desired and advantageous for any given or particular application. Furthermore, to the extent that the term "includes" is used in either the detailed description or the claims, such term is intended to be inclusive in a manner similar to the term "comprising."

What is claimed is:

1. A system that facilitates extraction of line edge roughness measurements that are independent of proprietorship of a metrology device, comprising:
   a structure patterned onto silicon with known line edge roughness values associated therewith;
   a metrology device that obtains line edge roughness measurements from the structure;
   a component that generates an inverse function based upon a comparison between the known line edge roughness values and the measured line edge roughness values; and
   a second structure patterned upon the silicon with unknown line edge roughness, the metrology device obtains line edge roughness measurements from the structure with unknown line edge roughness and applies the inverse function thereto.

2. The system of claim 1, an integrated circuit manufacturing process controlled based at least in part upon values output by the inverse function.

3. The system of claim 2, the integrated circuit manufacturing process being one of an etching process and a lithography process.

4. The system of claim 1, wherein line edge roughness of the second structure is corrected based at least in part upon values output by the inverse function.

5. The system of claim 1, the structure patterned onto the silicon is one of a square wave structure, a rectangular wave structure, and a sawtooth wave structure.

6. The system of claim 5, the line edge roughness measurements comprising one or more of amplitude of the square wave structure, wavelength of the square wave structure, pitch resident upon the square wave structure, amplitude of the rectangular wave structure, wavelength of the rectangular wave structure, pitch resident upon the rectangular wave structure, amplitude of the sawtooth structure, and wavelength of the sawtooth structure.

7. The system of claim 1, the metrology device employs a scanning electron microscope to obtain measurements of line edge roughness.

8. The system of claim 1, the metrology device employs scatterometry techniques to obtain measurements of line edge roughness.

9. The system of claim 1, the structure patterned onto the silicon is a reliability structure with known line edge roughness embedded therein.

10. The system of claim 8, the reliability structure being one of a comb and a serpentine reliability structure.

11. The system of claim 1, the structure patterned into the silicon being one of a library of structures with known line edge roughness values.

12. The system of claim 10, the library of structures with known line edge values is accessible over a network.

13. The system of claim 1, the structure patterned into the silicon via a reticle and lithography techniques.

14. A system that facilitates measuring of line edge roughness, comprising:
   means for patterning a structure with known line edge roughness values on a wafer;
   means for storing the line edge roughness values and correlating the line edge roughness values to the structure;
   means for employing a metrology device to obtain measurements of line edge roughness on the wafer;
   means for generating a correcting function based upon a comparison between the stored values and the measured values; and
   means for employing the correcting function to correct measurements made by the metrology device related to structures with unknown line edge roughness values.

15. The system of claim 14, further comprising means for modifying an integrated circuit manufacturing process to correct line edge roughness values based at least in part upon the corrected measurements.

16. A system for obtaining line edge roughness values, comprising:
- a metrology device that measures line edge roughness on a structure;
- a correcting component that compares the measured line edge roughness values to values previously stored within a data store, the correcting component generates an inverse function based at least in part upon a comparison between the measured line edge roughness and the stored values; and
- a second structure, the metrology device measures line edge roughness resident upon the second structure and applies the inverse function to the measured line edge roughness values to generate line edge roughness values that are independent of proprietorship of the metrology device.

* * * * *